United States Patent
Takeuchi et al.

(10) Patent No.: US 12,257,324 B2
(45) Date of Patent: Mar. 25, 2025

(54) SEMICONDUCTOR SWCNT SLURRY FOR BIOIMAGING AND METHOD FOR INSPECTING THE SAME

(71) Applicants: SHIMADZU CORPORATION, Kyoto (JP); NATIONAL INSTITUTE OF ADVANCED INDUSTRIAL SCIENCE AND TECHNOLOGY, Tokyo (JP)

(72) Inventors: Tsukasa Takeuchi, Kyoto (JP); Toshiya Okazaki, Ibaraki (JP); Yoko Iizumi, Ibaraki (JP); Hiromichi Kataura, Ibaraki (JP); Masako Yudasaka, Ibaraki (JP)

(73) Assignees: SHIMADZU CORPORATION, Kyoto (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 609 days.

(21) Appl. No.: 16/764,590

(22) PCT Filed: Nov. 17, 2017

(86) PCT No.: PCT/JP2017/041565
§ 371 (c)(1),
(2) Date: May 15, 2020

(87) PCT Pub. No.: WO2019/097698
PCT Pub. Date: May 23, 2019

(65) Prior Publication Data
US 2020/0384127 A1     Dec. 10, 2020

(51) Int. Cl.
*B32B 9/00* (2006.01)
*A61K 49/00* (2006.01)
(Continued)

(52) U.S. Cl.
CPC ...... *A61K 49/0065* (2013.01); *A61K 49/0019* (2013.01); *A61K 49/0076* (2013.01);
(Continued)

(58) Field of Classification Search
CPC ....... Y10T 428/30; B82Y 30/00; B82Y 40/00; Y10S 977/742; C01B 32/158; C01B 32/174
(Continued)

(56) References Cited

U.S. PATENT DOCUMENTS 9,082,984 B2 * 7/2015 Chan ...................... C08K 3/041
9,486,772 B1 * 11/2016 Lebron-Colon ...... C01B 32/174
(Continued)

FOREIGN PATENT DOCUMENTS

JP          2006-182657 A      7/2006
JP          2012-32358 A       2/2012
(Continued)

OTHER PUBLICATIONS

Saunab Ghosh et al., "Oxygen Doping Modifies Near-Infrared Band Gaps in Fluorescent Single-Walled Carbon Nanotubes", Science, Dec. 17, 2010, pp. 1656-1659, vol. 330.
(Continued)

*Primary Examiner* — Daniel H Miller
(74) *Attorney, Agent, or Firm* — Sughrue Mion, PLLC

(57) ABSTRACT

An object is to provide a method of inspection enabling a slurry of a batch resulting in abnormal accumulation to be identified in advance, and to provide an SWCNT slurry for bioimaging that has undergone the inspection.
In order to solve the above problems, the present invention provides a method for inspecting a semiconductor single-walled carbon nanotube (SWCNT) slurry for bioimaging, the slurry comprising: semiconductor SWCNTs oxidized by being directly irradiated with ultraviolet rays in atmosphere
(Continued)

and a dispersant composed of an amphiphilic substance that coats surfaces of the SWCNTs, the method comprising: using at least two types of methods selected from the group consisting of absorption spectroscopy, a photoluminescence method, and particle size measurement, confirming that an average particle size of the semiconductor SWCNTs is smaller than 10 nm, isolated dispersibility of the semiconductor SWCNTs is high, and/or the semiconductor SWCNTs are oxidized.

2 Claims, 5 Drawing Sheets

(51) Int. Cl.
    *C01B 32/159* (2017.01)
    *C01B 32/174* (2017.01)
    *B82Y 5/00* (2011.01)
    *B82Y 20/00* (2011.01)
    *B82Y 40/00* (2011.01)

(52) U.S. Cl.
    CPC .......... *C01B 32/159* (2017.08); *C01B 32/174* (2017.08); *B82Y 5/00* (2013.01); *B82Y 20/00* (2013.01); *B82Y 40/00* (2013.01); *C01B 2202/02* (2013.01); *C01B 2202/22* (2013.01); *C01P 2004/64* (2013.01); *Y10T 428/30* (2015.01)

(58) Field of Classification Search
    USPC ......................................................... 428/408
    See application file for complete search history.

(56) References Cited

U.S. PATENT DOCUMENTS

| | | | |
|---|---|---|---|
| 2004/0022718 A1* | 2/2004 | Stupp | C01B 32/168 423/445 R |
| 2008/0152593 A1 | 6/2008 | Iijima et al. | |
| 2014/0255291 A1* | 9/2014 | Marti-Arbona | D01D 5/06 423/447.2 |
| 2017/0335185 A1 | 11/2017 | Iizumi et al. | |

FOREIGN PATENT DOCUMENTS

| | | |
|---|---|---|
| WO | 2014/080519 A1 | 5/2014 |
| WO | 2016/117633 A1 | 7/2016 |

OTHER PUBLICATIONS

Yuhei Miyauchi et al., "Brightening of excitons in carbon nanotubes on dimensionality modification", Nature Photonics, Sep. 2013, pp. 715-719, vol. 7.

Masakazu Umezawa et al., "Mouseairway imaging by using near-infrared fluorescent carbon nanotube", Bioimaging, 2016, 5 pgs., vol. 25, No. 2.

International Search Report for PCT/JP2017/041565 dated Jan. 9, 2018 (PCT/ISA/210).

Written Opinion of the International Searching Authority for PCT/JP2017/041565 dated Jan. 9, 2018 (PCT/ISA/237).

Robinson et al., "In Vivo Fluorescence Imaging in the Second Near-Infrared Window with Long Circulating Carbon Nanotubes Capable of Ultrahigh Tumor Uptake", J. Am. Chem. Soc., 2012, vol. 134, pp. 10664 to 10669 (6 pages total).

Notice of Reasons for Refusal dated Nov. 2, 2021 from the Japanese Patent Office in JP Application No. 2019-553648.

Office Action dated Nov. 7, 2022 issued by the Chinese Patent Office in Chinese Application No. 201780096900.2.

Office Action dated Apr. 22, 2023 from the Chinese Patent Office in Application No. 201780096900.2.

Office Action dated May 30, 2022, issued in Chinese Application No. 201780096900.2.

* cited by examiner

SEMICONDUCTOR SWCNT SLURRY FOR BIOIMAGING AND METHOD FOR INSPECTING THE SAME

CROSS REFERENCE TO RELATED APPLICATIONS

This application is a National Stage of International Application No. PCT/JP2017/041565 filed Nov. 17, 2017.

TECHNICAL FIELD

The present invention relates to a semiconductor single-walled carbon nanotube (SWCNT) slurry for bioimaging and a method for inspecting the same.

BACKGROUND ART

Carbon nanotubes (hereinafter, also referred to as CNTs) refer to a carbon structure having a structure in which a carbon sheet (what is known as a graphite sheet), having carbon atoms in hexagonal planer arrangement, is closed to be in a cylindrical form. The CNTs include multi-walled and single-walled CNTs. The single-walled CNTs (hereinafter, also referred to as SWCNTs) are known to have electronic properties depending on how they are wound (diameter and spiral degree), meaning that they exhibit either metallic property or semiconducting property.

Semiconductor SWCNTs absorb and emit light in a near-infrared region (800 to 2000 nm) with good biological penetration, and thus are expected to be useful as fluorescent probes for detecting the functions of cells and living organisms. In particular, the wavelength region of 1200 to 1400 nm is a region with the best biological penetration.

The emission wavelength can be changed by introducing oxygen atoms or functional groups into the semiconductor SWCNTs. For example, a technique is known in which water containing ozone is mixed with an aqueous solution in which SWCNTs are dispersed with a surfactant, and a chemical reaction is performed with light irradiation to partially replace carbon in the nanotube walls with oxygen atoms (Non Patent Literatures 1 and 2). When oxygen atoms are introduced in this manner, most of the oxygen atoms are ether-bonded to the walls of the SWCNTs, and the emission energy of the SWCNTs becomes about 150 meV smaller than the original emission energy. Such chemical modification also has the advantage of increasing the emission quantum yield of SWCNTs.

However, as for the longer emission wavelength reported in Non Patent Literatures 1 and 2, an SWCNT having a chiral index (6,5), which is one of the most studied SWCNTs at present, the emission wavelength having a peak at about 1140 nm (about 1.088 eV) is predominant. It is shorter than about 1300 nm to 1400 nm, which is known to be most preferred as near-infrared fluorescent probes.

Patent Literature 1 discloses a method for producing near-infrared light emitting semiconductor single-walled carbon nanotubes that includes irradiating semiconductor single-walled carbon nanotubes directly with ultraviolet rays in the atmosphere to generate ozone and oxidize the semiconductor single-walled carbon nanotubes.

According to Patent Literature 1, oxygen atoms can be easily introduced into the SWCNTs in the order of grams in a short time, and the emission wavelength peak can be changed from 980 nm (1.265 eV) to 1280±13 nm (0.9686±0.01 eV).

CITATION LIST

Patent Literature

Patent Literature 1: International Publication No. 2016/117633

Non Patent Literature

Non Patent Literature 1: Ghosh et al., Science, 330, 1656-1659 (2010).
Non Patent Literature 2: Miyauchi et al., Nat. Photonics, 7, 715-719 (2013).

SUMMARY OF INVENTION

Technical Problem

However, when using semiconductor SWCNTs manufactured by the method described in Patent Literature 1 described above to prepare a slurry for bioimaging (probe for living organisms) to be administered to a living organism (mouse), there is a problem in that the quality varies among batches meaning that a constant level of performance cannot be obtained. For example, for some batches, dispersion of the semiconductor SWCNTs may be insufficient. In such a case, there is a problem in that accumulation in a specific site (especially the liver) occurs in a short period of time, resulting in a failure to detect the fluorescence distribution in other regions. Furthermore, the aggregation of SWCNTs in a living organism also leads to a risk of clogging in the lungs and the like, which could be fatal. Thus, it has been necessary to determine a degree of variation of the quality among batches before administration to a living organism, preferably before shipment.

In view of the above-mentioned circumstances, an object of the present invention is to provide a method of inspection enabling a slurry of a batch failed to achieve a certain performance (such as one resulting in abnormal accumulation or not emitting light in a predetermined wavelength range) to be identified in advance, and to provide an SWCNT slurry for bioimaging that has undergone the inspection.

Solution to Problem

As a result of intensive studies, the inventors of the present invention have found that a slurry resulting in SWCNT accumulation in the liver cannot be excluded by measuring the properties of the SWCNTs with a single method when evaluating the SWCNT slurry for bioimaging, but a batch of slurry resulting in abnormal accumulation can be determined by executing a combination of a plurality of predetermined analysis methods. Specifically, the gist of the present invention is as follows.

(1) A bioimaging semiconductor single-walled carbon nanotube (SWCNT) slurry comprising a semiconductor SWCNT slurry including semiconductor SWCNTs oxidized by being directly irradiated with ultraviolet rays in atmosphere and a dispersant composed of an amphiphilic substance that coats surfaces of the semiconductor SWCNTs, wherein
the bioimaging semiconductor SWCNT slurry consisting only of the semiconductor SWCNT slurry that has been confirmed, using at least two types of methods selected from the group consisting of absorption spectroscopy, a photoluminescence method, and particle size measurement, that an average particle size of the semiconductor SWCNTs is smaller than 10 nm, isolated dispersibility of the semiconductor SWCNTs is high, and/or the semiconductor SWCNTs are oxidized.

(2) The semiconductor SWCNT slurry for bioimaging according to the above (1), wherein the particle size measurement is measurement by a centrifugal sedimentation method.

(3) A method for inspecting a semiconductor single-walled carbon nanotube (SWCNT) slurry for bioimaging, the slurry comprising: semiconductor SWCNTs oxidized by being directly irradiated with ultraviolet rays in atmosphere and a dispersant composed of an amphiphilic substance that coats surfaces of the SWCNTs, the method comprising:

using at least two types of methods selected from the group consisting of absorption spectroscopy, a photoluminescence method, and particle size measurement, confirming that an average particle size of the semiconductor SWCNTs is smaller than 10 nm, isolated dispersibility of the semiconductor SWCNTs is high, and/or the semiconductor SWCNTs are oxidized.

(4) The method for inspecting a semiconductor SWCNT slurry for bioimaging according to the above (3), wherein the particle size measurement is measurement by a centrifugal sedimentation method.

Advantageous Effects of Invention

By using two or more of the absorption spectroscopy, the photoluminescence method, and the particle size measurement, the inspection method according to the present invention enables a slurry of a batch failed to achieve a certain performance (such as one resulting in abnormal accumulation or not emitting light in a predetermined wavelength region) to be identified in advance and can provide a desired SWCNT slurry for bioimaging.

DESCRIPTION OF EMBODIMENTS

Figure 1:
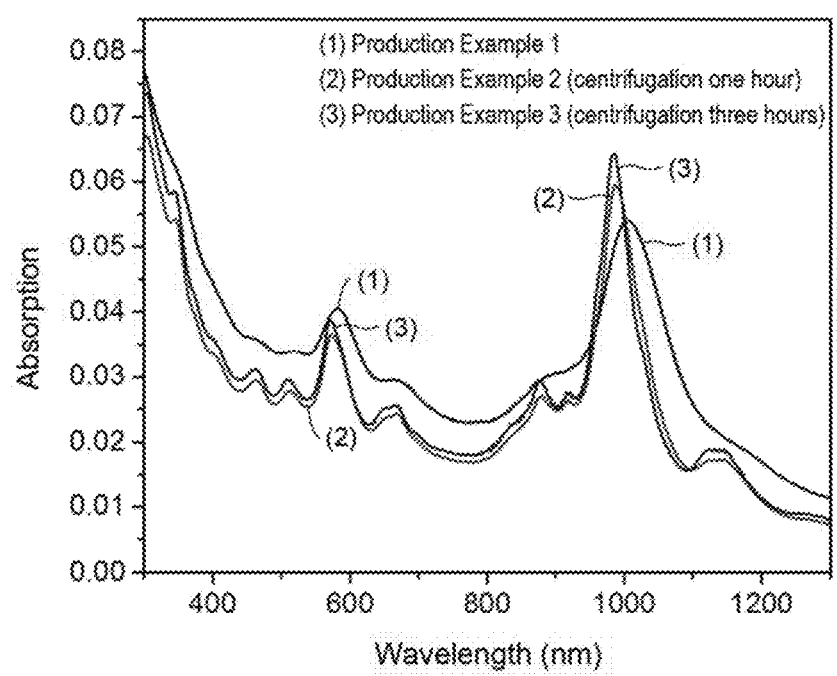
FIG. 1 is a diagram showing absorption spectra of semiconductor SWCNT slurrys for bioimaging in Production Examples 1 to 3.

Hereinafter, the present invention will be described in detail.

A semiconductor SWCNT slurry for bioimaging serving as an inspection target of a method according to the present invention includes semiconductor SWCNTs oxidized by direct irradiation with ultraviolet rays in the atmosphere and a dispersant composed of an amphiphilic substance that coats the surfaces of the semiconductor SWCNTs.

By direct irradiation with ultraviolet rays in the atmosphere, ozone is generated and oxygen atoms are introduced into the semiconductor SWCNTs. The semiconductor SWCNTs obtained by direct irradiation with ultraviolet rays in the atmosphere can shift the emission energy to the low energy side by 296±10 meV. Especially when applied to SWCNTs having a chiral index (6,5), the emission wavelength peak changes from about 980 nm to 1280±13 nm, and thus the emission wavelength has its peak in a wavelength region having biological penetration, which is preferable as a near-infrared fluorescent probe.

Regarding the oxidation treatment by irradiation with ultraviolet rays, in the conventional wet method (method for reacting SWCNTs in an aqueous solution) such as Non Patent Literatures 1 and 2 described above, most oxygen is ether-bonded with SWCNTs, and low energy shifts exceeding 290 meV is difficult. In contrast, into the semiconductor SWCNTs serving as an evaluation target of the present invention, by being directly irradiated with ultraviolet rays in the atmosphere, most of the introduced oxygen atoms are introduced as an epoxide, which enables a shift of the emission energy of the SWCNTs to the low energy side of by 296±10 meV.

The method for synthesizing the semiconductor SWCNTs is not particularly limited, and the semiconductor SWCNTs can be synthesized as appropriate using a known method such as a chemical vapor deposition method, an arc discharge method, and a laser evaporation method. In particular, it is preferable to synthesize the semiconductor SWCNTs by a chemical vapor deposition method in the presence of a catalyst.

The average particle size of the semiconductor SWCNTs in the slurry is preferably smaller than 10 nm, and is preferably in the range of 6 nm or more and less than 10 nm. Micro semiconductor SWCNTs having an average particle size of less than 10 nm cause no clogging in blood vessels in the lungs and the like, and have low toxicity. Here, the average particle size of the semiconductor SWCNTs refers to an average diameter in a weight-based particle size distribution measured by a centrifugal sedimentation method.

To generate ozone by direct irradiation with ultraviolet rays in the atmosphere, it is preferable to perform the ozone generation in a closed space. For example, a device that generates ozone by irradiating the atmosphere with ultraviolet rays, such as a UV ozone cleaner, is preferably used. Irradiation conditions of ultraviolet rays vary depending on an apparatus used, and it is preferable that the irradiation is performed under conditions that the semiconductor SWCNTs are not destroyed by the irradiation.

In addition, in order to directly irradiate the semiconductor SWCNTs with ultraviolet rays in the atmosphere, it is preferable to previously form the semiconductor SWCNTs in a film on a base material. In particular, in order to cause an even chemical reaction in the semiconductor SWCNTs into which oxygen atoms are introduced, it is preferable to irradiate the semiconductor SWCNTs formed into a thin film having a thickness of about 1 μm with ultraviolet rays.

The dispersant composed of an amphiphilic substance that coats the surfaces of the semiconductor SWCNTs is not particularly limited, and any dispersant may be used as appropriate as long as it has low toxicity to living organisms and has excellent affinity with the semiconductor SWCNTs. Specific examples include polyethylene glycol lipid derivatives in which hydrophilic PEG is bonded to a hydrophobic lipid site, nucleic acids, bovine serum albumin, and the like. In particular, polyethylene glycol lipid derivatives such as distearoyl-phosphatidylethanolamine-PEG2000 (DSPE-PEG$_{2000}$) are preferably used.

By coating the surfaces of the semiconductor SWCNTs with a dispersant such as DSPE-PEG$_{2000}$, the dispersion state of the semiconductor SWCNTs is maintained. In addition, the semiconductor SWCNTs have a micro particle size. Thus, the semiconductor SWCNTs cause no accumulation in a specific organ or no clogging in blood vessels of the lungs and the like.

The weight ratio of the oxidized semiconductor SWCNTs to the dispersant composed of an amphiphilic substance is not particularly limited as long as the surfaces of the semiconductor SWCNTs is sufficiently coated and the dispersion state can be maintained. It is preferable that the weight ratio of the oxidized semiconductor SWCNTs to the dispersant is in the range of 1:2 to 1:20.

Various methods can be used to produce the semiconductor SWCNT slurry for bioimaging as described above. First, as described above, it is preferable to disperse the semiconductor SWCNTs, oxidized by direct irradiation with ultraviolet rays in the atmosphere, in a surfactant solution before the surface is coated with a dispersant.

Here, the surfactant may be any one that can disperse the semiconductor SWCNTs, and can be selected for use from various known surfactants such as an anionic surfactant, a cationic surfactant, an amphoteric ionic surfactant, and a nonionic surfactant.

Examples of the anionic surfactant include alkyl benzene sulfonate, alkyl naphthalene sulfonate, alkyl sulfonate, di alkyl sulfosuccinate, alkyl sulfate, polyoxyethylene alkyl ether sulfate, alkyl phosphate, polyoxyethylene alkyl ether phosphate, cholate, deoxycholate, glycocholate, taurocholate, and taurodeoxycholate.

Examples of the cationic surfactant include tetraalkylammonium salts, trialkylbenzylammonium salts, and alkylpyridinium salts.

Examples of the amphoteric surfactants include amphoteric polymers such as 2-methacryloyloxyphosphorylcholine polymers and polypeptides, 3-(N,N-dimethylstearylammonio)-propanesulfonate, 3-(N,N-dimethylstearylammonio) propanesulfonate, 3-(N,N-dimethylmyristylammonio) propanesulfonate, 3-[(3-cholamidopropyl) dimethylammonio] propanesulfonate (CHAPS), 3-[(3-cholamidopropyl) dimethylammonio]-2-hydroxypropanesulfonate (CHAPSO), n-dodecyl-N,N'-dimethyl-3-ammonio-1-propanesulfonate, n-hexadecyl-N,N'-dimethyl-3-ammonio-1-propanesulfonate, n-octylphosphocholine, n-dodecylphosphocholine, n-tetradecylphosphocholine, n-hexadecylphosphocholine, dimethylalkyl betaine, perfluoroalkyl betaine, and N,N-bis(3-D-gluconamide propyl)-cholamido, and lecithin.

Examples of the nonionic surfactant include polyoxyethylene alkyl ether, polyoxyethylene alkyl phenyl ether, polyoxyethylene polyhydric alcohol fatty acid partial ester, and polyglycerin fatty acid ester.

In particular, alkylbenzene sulfonates such as sodium lauryl benzenesulfate (SDBS) are preferably used because of their excellent dispersibility for semiconductor SWCNTs.

As a method for dispersing the semiconductor SWCNTs in a surfactant solution, various kinds of homogenizers and the like can be used.

The obtained slurry may be subjected to centrifugation as necessary, and the supernatant is collected, so that the isolated dispersibility of the semiconductor SWCNTs can be enhanced. The isolated and dispersed semiconductor single-walled SWCNTs are preferable because they have advantages of improvement in fluorescence quantum yield, observability, and clearance when administered to living organisms.

Subsequently, a dispersant composed of an amphiphilic substance, such as the above-mentioned polyethylene glycol lipid derivatives, is dissolved in the slurry obtained by dispersing the semiconductor SWCNTs in the surfactant solution, and thereafter, the surfactant is removed from the resulting solution by dialysis. As a result, the surfactant existing around the semiconductor SWCNTs is replaced with a dispersant such as a polyethylene glycol lipid derivative, and the surfaces of the semiconductor SWCNTs can be sufficiently coated with the dispersant.

When the semiconductor SWCNTs whose surface is coated with the dispersant are administered to a living organism as a semiconductor SWCNT slurry for bioimaging, the dispersion state is maintained. In addition, the semiconductor SWCNTs have a micro particle size. Thus, the semiconductor SWCNTs cause no accumulation in a specific organ (mainly the liver), whereby halation can be reduced. In addition, the semiconductor SWCNTs cause no clogging in blood vessels of the lungs and the like, and the surfactant such as SDBS and the like is removed by dialysis, whereby the toxicity is extremely low. In addition, since the semiconductor SWCNTs are dispersed well, their cohesiveness is reduced, whereby a decrease in the emitted fluorescence intensity can be prevented.

In the present invention, the semiconductor SWCNT slurry for bioimaging as described above is inspected using at least two types of methods selected from the group consisting of absorption spectroscopy, a photoluminescence method, and particle size measurement.

Here, as the absorption spectroscopy, a method using infrared rays, visible rays, ultraviolet rays, or the like can be adopted. With this method, the SWCNT concentration and dispersion states in the slurry can be evaluated.

A light source, a stage, a detector, and the like forming a measurement system for the photoluminescence method (PL method) may each have a general configuration. Still, the light emitted in a near-infrared range is preferably detected with the excitation wavelength set to be within a range of 400 nm to 1000 nm (980 nm, for example), so that semiconductor SWCNTs are oxidized and light emission in a wavelength region of 1200 to 1400 nm featuring excellent biological penetration can be confirmed.

Furthermore, as a method for the particle size measurement, a method such as an image analysis method, a centrifugal sedimentation method, and a laser diffraction scattering method can be adopted as appropriate. In particular, the particle size measurement is preferably implemented using the centrifugal sedimentation method with which a weight-based particle size distribution can be obtained. This method enables whether the average particle size of semiconductor SWCNTs is smaller than 10 µm so as not to clog vessels in the lungs and the like and whether high isolated dispersibility is achieved to be determined, and also enables the percentage of particles smaller than 10 nm in the particle size distribution of semiconductor SWCNTs to be evaluated.

It is important for the semiconductor SWCNT slurry for bioimaging to exhibit the following properties when administered to a living organism: no aggregation; fluorescence can be monitored in a region other than a specific organ; and fluorescence intensity is high. It would be inappropriate to evaluate such properties specific to a slurry for bioimaging, using only one of the absorption spectroscopy, the photoluminescence method, and the particle size measurement. Thus, comprehensive evaluation needs to be performed with at least two types of these combined. Preferably, the particle size measurement is combined with the absorption spectroscopy and/or the photoluminescence method. This makes it possible to provide the SWCNT slurry for bioimaging while maintaining good performance maintained with no variation in quality.

EXAMPLES

Hereinafter, the present invention will be described in more detail with reference to examples, but the present invention is not limited to these examples.

Production Example 1

To 10 ml of ethanol, 1 mg of carbon nanotubes (CoMo-CAT SG65i, average diameter 0.8 nm, hereinafter referred to as "semiconductor SWCNTs") was added, and the semiconductor SWCNTs were dispersed in ethanol by bath sonication for about 5 minutes. Subsequently, an omnipore membrane ($\varphi$47 mm, 5 μm pore was set in a reduced pressure filter, a semiconductor SWCNT/ethanol slurry was put therein and filtered, and the semiconductor SWCNTs were uniformly placed on the filter. Next, the semiconductor SWCNTs remaining on the filter were placed in between sheets of medical paper, and dried at 60° C. for 30 minutes while being weighted lightly so that the filter was not rolled up. Then, the semiconductor SWCNTs placed on the filter were ozone-treated together with the filter for 60 to 70 seconds (the light source was a mercury lamp, and the ultraviolet intensity on the semiconductor SWCNTs was about 19 mW/cm$^2$).

After the ozone treatment, the semiconductor SWCNTs together with the filter were put in 10 ml of 0.3% distearoylphosphatidylethanolamine-PEG2000 (DSPE-PEG$_{2000}$) and sonicated for 20 minutes (ON:OFF=1 second:1 second) while being cooled with ice using a tip-type homogenizer, whereby the semiconductor SWCNTs were dispersed in the DSPE-PEG$_{2000}$ solution. Subsequently, the semiconductor SWCNT dispersion solution from which the filter was removed was applied to an ultracentrifuge (104,000 g, 3 hours), and the supernatant was collected to produce a semiconductor SWCNT slurry for bioimaging.

Production Example 2

To 10 ml of ethanol, 1 mg of carbon nanotubes (CoMo-CAT SG65i, average diameter 0.8 nm, hereinafter referred to as "semiconductor SWCNTs") was added, and the semiconductor SWCNTs were dispersed in ethanol by bath sonication for about 5 minutes. Subsequently, an omnipore membrane ($\varphi$47 mm, 5 μm pore was set in a reduced pressure filter, a semiconductor SWCNT/ethanol slurry was put therein and filtered, and the semiconductor SWCNTs were uniformly placed on the filter. Next, the semiconductor SWCNTs remaining on the filter were placed in between sheets of medical paper, and dried at 60° C. for 30 minutes while being weighted lightly so that the filter was not rolled up. Then, the semiconductor SWCNTs placed on the filter were ozone-treated together with the filter for 60 to 70 seconds (the light source was a mercury lamp, and the ultraviolet intensity on the semiconductor SWCNTs was about 19 mW/cm$^2$).

After the ozone treatment, the semiconductor SWCNTs together with the filter were put in 10 ml of 1% SDBS-H$_2$O and sonicated for 20 minutes (ON:OFF=1 second:1 second) while being cooled with ice using a tip-type homogenizer, whereby the semiconductor SWCNTs were dispersed in the SDBS solution. Subsequently, the semiconductor SWCNT dispersion solution from which the filter was removed was applied to an ultracentrifuge (104,000 g, 1 hour), and the supernatant was collected to obtain a semiconductor SWCNT isolated slurry.

Distearoyl phosphatidylethanolamine-PEG2000 (DSPE-PEG$_{2000}$) was added to the semiconductor SWCNT isolated slurry at a concentration of 3 mg/ml, and the powder of DSPE-PEG$_{2000}$ was dissolved by bath sonication for about 5 minutes. Then, this solution was put into a dialysis membrane (Spectrum, G235070), and dialyzed against 2 liters of water. In this process, SDBS was replaced with DSPE-PEG$_{2000}$.

Two hours later, 5 ml of the external dialysate was set aside for analysis and the remaining dialysate was discarded and replaced with water. Similarly, after one night, two days, and three days, the water was replaced with new one, and the dialysis rate was calculated by measuring the absorption spectrum of the external dialysate set aside for analysis. The dialysis was ended when the elution of SDBS of 95% or more was observed, and a target semiconductor SWCNT slurry for bioimaging was produced.

Production Example 3

To 10 ml of ethanol, 1 mg of carbon nanotubes (CoMo-CAT SG65i, average diameter 0.8 nm, hereinafter referred to as "semiconductor SWCNTs") was added, and the semiconductor SWCNTs were dispersed in ethanol by bath sonication for about 5 minutes. Subsequently, an omnipore membrane ($\varphi$47 mm, 5 μm pore was set in a reduced pressure filter, a semiconductor SWCNT/ethanol slurry was put therein and filtered, and the semiconductor SWCNTs were uniformly placed on the filter. Next, the semiconductor SWCNTs remaining on the filter were placed in between sheets of medical paper, and dried at 60° C. for 30 minutes while being weighted lightly so that the filter was not rolled up. Then, the semiconductor SWCNTs placed on the filter were ozone-treated together with the filter for 60 to 70 seconds (the light source was a mercury lamp, and the ultraviolet intensity on the semiconductor SWCNTs was about 19 mW/cm$^2$).

After the ozone treatment, the semiconductor SWCNTs together with the filter were put in 10 ml of 1% SDBS-H$_2$O and sonicated for 20 minutes (ON:OFF=1 second:1 second) while being cooled with ice using a tip-type homogenizer, whereby the semiconductor SWCNTs were dispersed in the SDBS solution. Subsequently, the semiconductor SWCNT dispersion solution from which the filter was removed was applied to an ultracentrifuge (104,000 g, 3 hours), and the supernatant was collected to obtain a semiconductor SWCNT isolated slurry.

Distearoyl phosphatidylethanolamine-PEG2000 (DSPE-PEG$_{2000}$) was added to the semiconductor SWCNT isolated slurry at a concentration of 3 mg/ml, and the powder of DSPE-PEG$_{2000}$ was dissolved by bath sonication for about 5 minutes. Then, this solution was put into a dialysis membrane (Spectrum, G235070), and dialyzed against 2 liters of water. In this process, SDBS was replaced with DSPE-PEG$_{2000}$.

Two hours later, 5 ml of the external dialysate was set aside for analysis and the remaining dialysate was discarded and replaced with water. Similarly, after one night, two days, and three days, the water was replaced with new one, and the dialysis rate was calculated by measuring the absorption spectrum of the external dialysate set aside for analysis. The dialysis was ended when the elution of SDBS of 95% or more was observed, and a target semiconductor SWCNT slurry for bioimaging was produced.

(Measurement by Absorption Spectroscopy and Photoluminescence Method)

Figure 2:
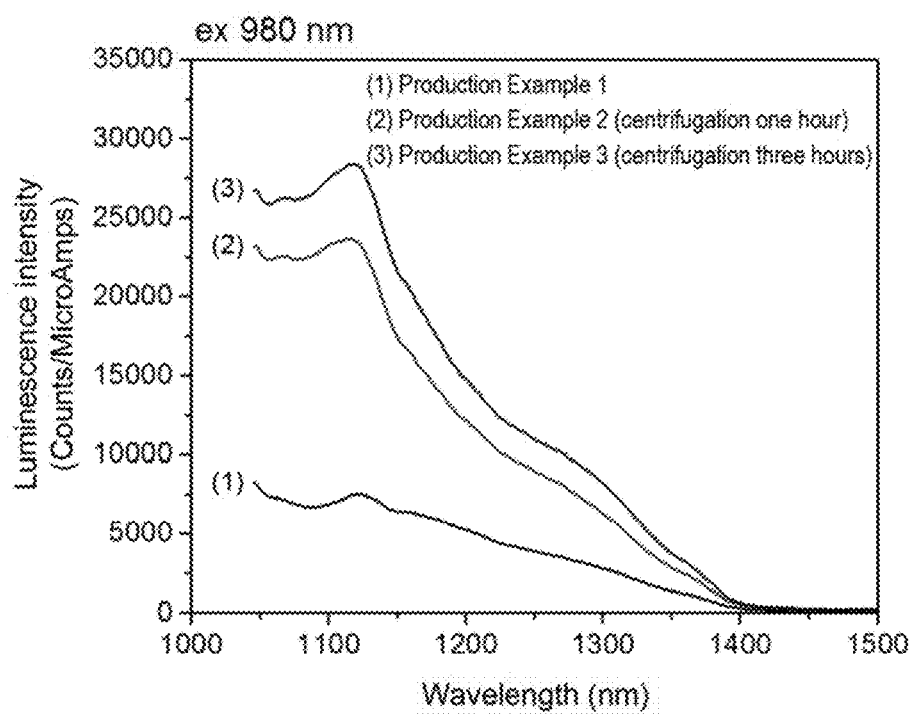
FIG. 2 is a diagram showing emission spectra of the semiconductor SWCNT slurrys for bioimaging in Production Examples 1 to 3.

The absorption spectra of the semiconductor SWCNT slurrys for bioimaging obtained in Production Examples 1 to 3 were measured using the UV-Vis-NIR spectrophotometer UV-3100 manufactured by Shimadzu Corporation. Furthermore, the emission spectra were measured using Fluorolog-3-2-iHR320 manufactured by HORIBA, Ltd., with the excitation wavelength set to be 980 nm. FIGS. 1 and 2 respectively show the results of these measurements. Note that the absorbance and luminescence intensity in FIGS. 1 and 2 are shown with the concentration of the slurry standardized.

As shown in FIG. 1, absorption peaks are found at 570 nm and 980 nm, and the line width is reduced due to centrifugation indicating that the rate of the SWCNTs isolated and dispersed is high. In addition, the shoulder at about 1300 nm in the emission spectra in FIG. 2 indicates that the semiconductor single-walled carbon nanotubes were oxidized by being directly irradiated with ultraviolet rays in the atmosphere, and particularly oxygen atoms were introduced as an epoxide.

Furthermore, as shown in FIG. 2, higher emission intensity was obtained with the semiconductor SWCNT slurrys in Production Examples 2 and 3, which had undergone the step of dispersing the semiconductor SWCNTs in a solution of a surfactant (SDBS), compared with the semiconductor SWCNT slurry in Production Example 1 manufactured without such a process, that is, with the semiconductor SWCNTs directly dispersed in DSPE-$PEG_{2000}$. This feature of Production Examples 2 and 3 is expected to be a result of improvement in emission quantum efficiency due to higher isolated dispersibility attributable to sufficient coating of the surfaces of the semiconductor SWCNTs with DSPE-$PEG_{2000}$, compared with Production Example 1, leading to no aggregation of the semiconductor SWCNTs.

As shown in FIG. 1, the absorption wavelengths of Production Examples 2 and 3 were shifted to the lower wavelength side as compared with Production Example 1. This is expected to be due to an increased ratio of the SWCNTs in the isolated dispersion state to the bundled SWCNTs.

(Particle Size Measurement)

Figure 3:
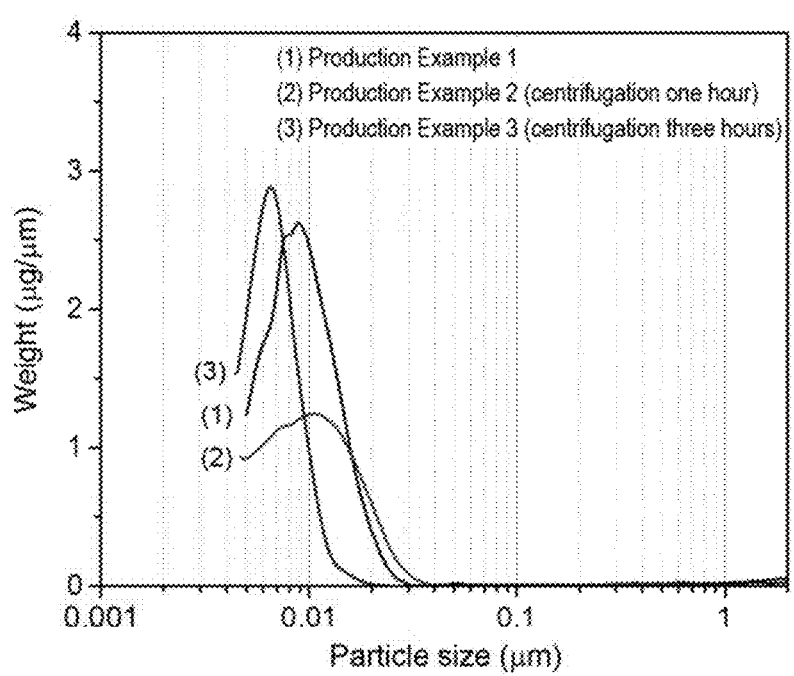
FIG. 3 is a diagram showing particle size distributions of semiconductor SWCNTs in the semiconductor SWCNT slurrys for bioimaging in Production Examples 1 to 3.

Particle size measurement was performed on the semiconductor SWCNT slurry for bioimaging obtained in Production Examples 1 to 3 by the centrifugal sedimentation method, using a disk centrifugal particle size distribution measuring device DC24000UHR manufactured by CPS. The results are shown in FIG. 3. The results in FIG. 3 show that the average particle sizes of the semiconductor SWCNTs in the semiconductor SWCNT slurrys for bioimaging in Production Examples 1 to 3 were 8 nm, 10 nm, and 6.5 nm, respectively. In addition, the percentages of particles having a particle size smaller than 10 nm in these semiconductor SWCNT slurrys for bioimaging were 44%, 30%, and 84%, respectively. It was confirmed that the semiconductor SWCNTs in Production Example 3, in which centrifugation was performed for 3 hours were more isolated and dispersed, compared with Production Example 2 in which centrifugation was performed for 1 hour.

(In Vivo Imaging)

The semiconductor SWCNT slurrys for bioimaging obtained in Production Example 3 and Production Example 1 were prepared with a 0.3% DSPE-PEG2000 solution so that the SWCNT concentration became 200 μg/ml, and 0.1 ml of the liquids was administered to mice. After 0 to 6 hours, the fluorescence was observed using the SAI-1000 apparatus manufactured by Shimadzu Corporation. The results are shown in FIG. 4 (Production Example 3) and FIG. 5 (Production Example 1).

Figure 4:
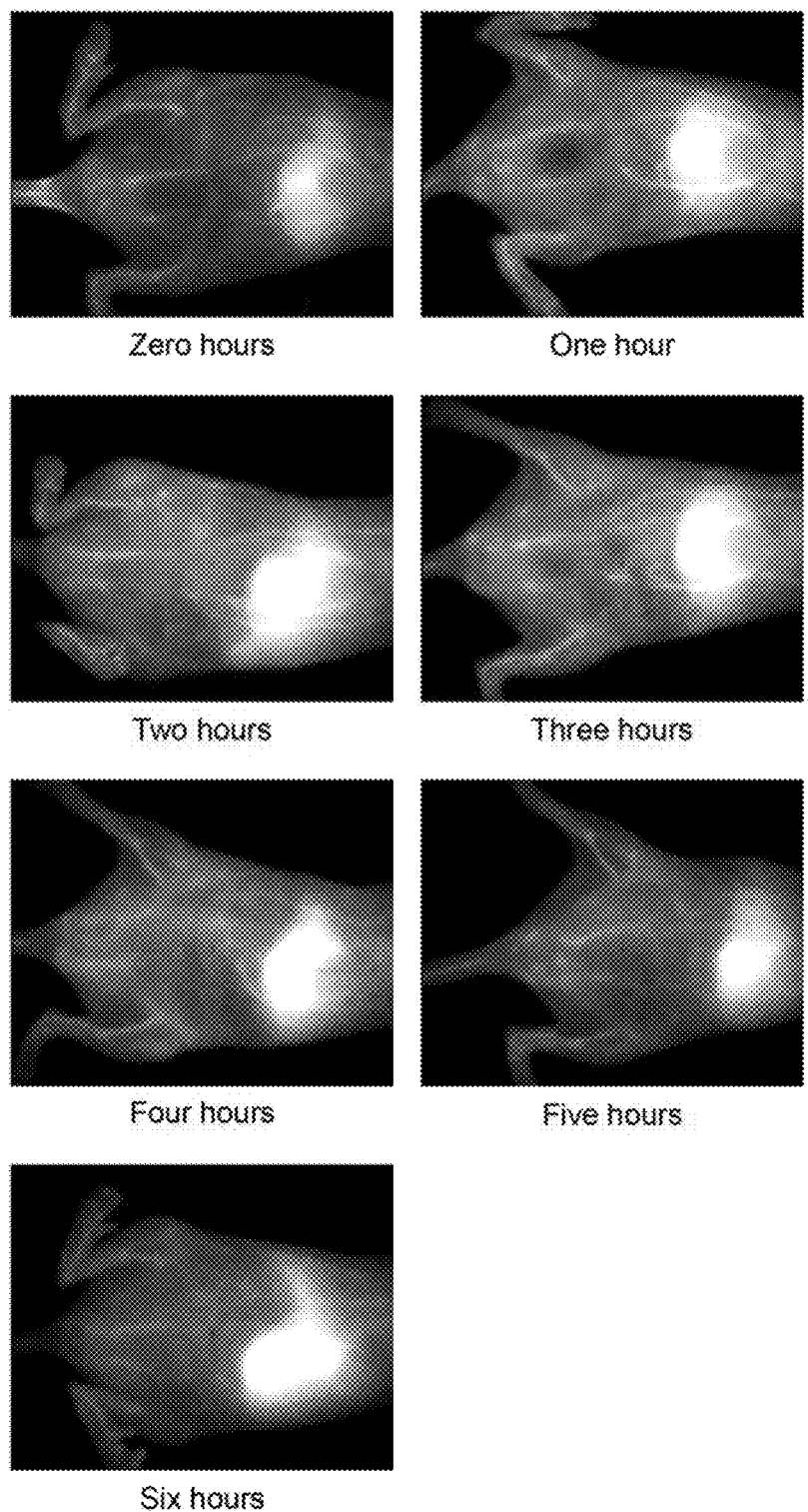
FIG. 4 is a view showing in vivo imaging in Production Example 3.
Figure 5:
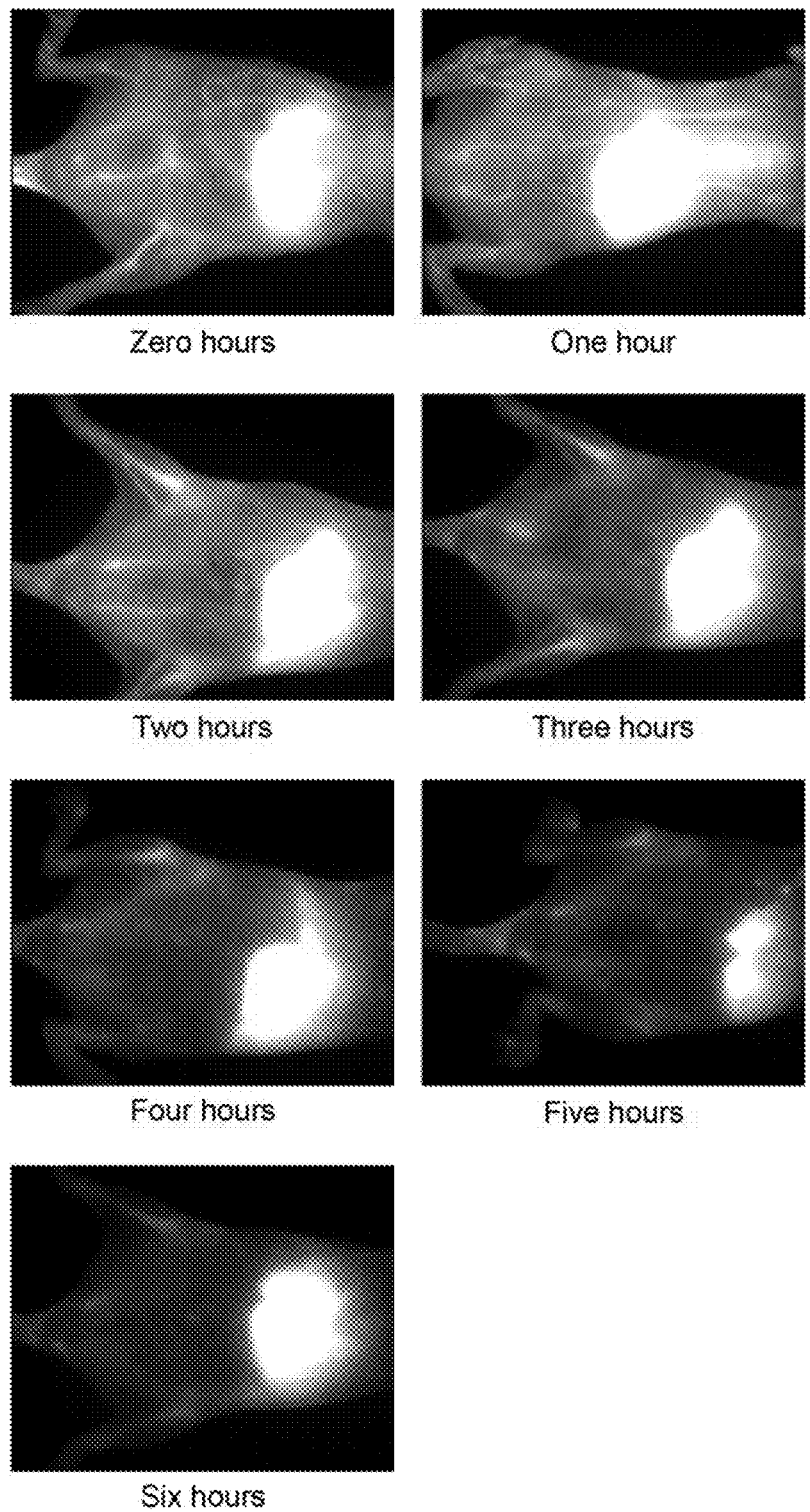
FIG. 5 is a view showing in vivo imaging in Production Example 1.

As shown in FIGS. 4 and 5, it is clear that, while accumulation of the semiconductor SWCNT slurry in Production Example 1 in the liver was observed, the semiconductor SWCNT slurry in Production Example 3 caused no accumulation observed in the liver even after a lapse of time after administration, and can thus reduce halation. Production Example 2 (not shown) also showed the same tendency as Production Example 1. This is thought to be because Production Example 1 does not include the process of dispersing the semiconductor SWCNTs in a solution of a surfactant (SDBS), and thus the isolated dispersibility was low, the coating with DSPE-$PEG_{2000}$ was insufficient, and the semiconductor SWCNTs were not dispersed well and partially aggregated.

As a result of measurement using the three methods including the absorption spectroscopy, the photoluminescence method, and the particle size measurement, the slurry obtained in Production Example 3 was determined to have satisfied the following conditions: (1) the average particle size of the semiconductor SWCNTs is smaller than 10 nm; (2) isolated dispersibility of the semiconductor SWCNTs is high; and (3) the semiconductor SWCNTs are oxidized.

On the other hand, in the case of Production Example 1, none of the above (1) to (3) was satisfied.

From the above, the inspection method according to the present invention can be considered as being effective as a method for determining whether a dispersant is obtained in a production example (batch) resulting in abnormal accumulation and failure to emit light in a desired wavelength region.

All publications, patent publications, and patent applications cited herein are hereby incorporated by reference in their entirety.

The invention claimed is:

1. A method for inspecting a semiconductor single-walled carbon nanotube (SWCNT) slurry for bioimaging, the slurry comprising: semiconductor SWCNTs oxidized by being directly irradiated with ultraviolet rays in atmosphere and a dispersant composed of an amphiphilic substance that coats surfaces of the SWCNTs, the method comprising:
    using at least two of absorption spectroscopy, a photoluminescence method, and particle size measurement, to confirm that an average particle size of the semiconductor SWCNTs is smaller than 10 nm, and the semiconductor SWCNTs are oxidized.

2. The method for inspecting a semiconductor SWCNT slurry for bioimaging according to claim 1, wherein the particle size measurement is measurement by a centrifugal sedimentation method.

* * * * *